United States Patent
Baras et al.

(10) Patent No.: US 9,341,623 B2
(45) Date of Patent: May 17, 2016

(54) IMMUNODIFFUSION ASSAY FOR INFLUENZA VIRUS

(75) Inventors: Benoit Guy Jules Baras, Rixensart (BE); Valerie Audry Micheline Jacob, Rixensart (BE)

(73) Assignee: GLAXOSMITHKLINE BIOLOGICALS SA (BE)

( * ) Notice: Subject to any disclaimer, the term of this patent is extended or adjusted under 35 U.S.C. 154(b) by 1070 days.

(21) Appl. No.: 13/497,339

(22) PCT Filed: Sep. 23, 2010

(86) PCT No.: PCT/EP2010/064075
§ 371 (c)(1),
(2), (4) Date: Mar. 21, 2012

(87) PCT Pub. No.: WO2011/036220
PCT Pub. Date: Mar. 31, 2011

(65) Prior Publication Data
US 2012/0178185 A1     Jul. 12, 2012

Related U.S. Application Data

(60) Provisional application No. 61/245,809, filed on Sep. 25, 2009.

(51) Int. Cl.
| | |
|---|---|
| *G01N 33/559* | (2006.01) |
| *G01N 33/569* | (2006.01) |
| *C07K 16/10* | (2006.01) |

(52) U.S. Cl.
CPC ........ *G01N 33/559* (2013.01); *G01N 33/56983* (2013.01); *C07K 16/1018* (2013.01); *G01N 2333/11* (2013.01)

(58) Field of Classification Search
CPC .......... G01N 33/559; G01N 33/56983; G01N 2333/11; C07K 16/1018
See application file for complete search history.

(56) References Cited

U.S. PATENT DOCUMENTS

| | | | |
|---|---|---|---|
| 7,873,227 B2 | 1/2011 | Geiger et al. | |
| 8,685,654 B2 * | 4/2014 | Sizer et al. | 435/7.1 |
| 2006/0051742 A1 * | 3/2006 | Kapteyn et al. | 435/5 |
| 2007/0141078 A1 * | 6/2007 | D'Hondt et al. | 424/204.1 |
| 2009/0092620 A1 | 4/2009 | Moste et al. | |
| 2009/0263470 A1 * | 10/2009 | Coller et al. | 424/450 |
| 2012/0178185 A1 * | 7/2012 | Baras et al. | 436/501 |

FOREIGN PATENT DOCUMENTS

| | | |
|---|---|---|
| EP | 0382271 B1 | 12/1994 |
| EP | 2014279 A1 | 1/2009 |
| WO | WO 02/28422 A2 | 4/2002 |
| WO | WO 2009/000433 A1 | 12/2008 |
| WO | WO 2009/081172 A1 | 7/2009 |

OTHER PUBLICATIONS

Bizhanov et al., 1988. Influence of detergents on measurement of influenza A virus haemagglutinin content in inactivated influenza vaccine by single radial immunodiffusion. Acta Virologica 32: 252-260.*
Johannsen et al., 1985. Quantification of haemagglutinin of influenza Tween-ether split vaccines by immunodiffusion. Vaccine 3 (Suppl.): 235-240.*
Williams, 1993. Single-radial-immunodiffusion as an in vitro potency assay for human inactivated viral vaccines. Veterinary Microbiology 37: 253-262.*
Willkommen et al., 1983. The influence of pH and ionic strength on the single radial immunodiffusion test in qualitative assay of influenza virus haemagglutinin. Acta Virologica 27: 407-411.*
Database Biosis, [Online] Jan. 1, 2008, Gao, et al., "Development of a method for determination of hemagglutinin content in pandemic influenza vaccine containing aluminium adjuvant", XP002519031 retrieved from BIOSIS PAN—PREV20080035107 ORD—2008-00-00 abstract.
Wood, et al., "An improved single radial immunodiffusion technique for the assay of influenza haemagglutinin antigen: Adaption for potency determination of inactivated whole virus and subunit vaccines", J. Biol. Stand. 5(3):237-247 (1977).
Wood, et al., "International collaborative study of single radial diffusion and immunoelectrophoresis techniques for the assay of haemagglutinin antigen of influenza virus", J. Biol. Stand. 9(3):317-330 (1981).
Xing, et al., "Single radial immunodiffusion as a method for the assay of the acellular pertussis vaccine components, pertussis toxoid, filamentous haemagglutinin and pertactin", Biologicals, 26(3):217-224 (1998).

* cited by examiner

*Primary Examiner* — Gail R Gabel
*Assistant Examiner* — James L Grun
(74) *Attorney, Agent, or Firm* — William T. Han; Jason C. Fedon

(57) ABSTRACT

A method for performing an immunodiffusion assay comprising at least the following steps of:
(a) preparing one or more test samples comprising an influenza virus antigen,
(b) treating the test samples with at least 5% (w/v) of detergent,
(c) applying the treated test samples to a gel comprising an antibody specific to the influenza virus antigen, and
(d) allowing the samples to diffuse into the gel.

15 Claims, No Drawings

IMMUNODIFFUSION ASSAY FOR INFLUENZA VIRUS

This application is the US National Stage of International Application No. PCT/EP2010/064075, filed 23 Sep. 2010, which claims benefit of the filing date of U.S. Provisional Application No. 61/245,809, filed 25 Sep. 2009. The disclosures of each of these applications are incorporated herein by reference.

TECHNICAL FIELD

The invention relates to the field of assays performed on virus preparations and vaccine compositions, such as compositions comprising influenza virus. In particular, the invention relates to the determination of antigen concentration in said preparations or compositions, particularly, in adjuvanted preparations and compositions, such as vaccines.

TECHNICAL BACKGROUND

Influenza viruses are one of the most ubiquitous viruses present in the world, affecting both humans and livestock. Influenza results in an economic burden, morbidity and even mortality, which are significant. Influenza viruses cause epidemics almost every winter, with infection virus rates as high as 40% over a six-week period. Influenza infection results in various disease states, from a sub-clinical infection through mild upper respiratory infection to a severe viral pneumonia. Typical influenza epidemics cause increases in incidence of pneumonia and lower respiratory disease as witnessed by increased rates of hospitalization or mortality.

Vaccination plays a critical role in controlling annual influenza epidemics. Currently available influenza vaccines are either inactivated or live attenuated influenza vaccines.

While the vast majority of current influenza vaccines, for seasonal flu, are non-adjuvanted vaccines, other approaches such as for pandemic vaccines rely on adjuvantation in order to be able to decrease the antigen content (antigen sparing) and thus increase the number of vaccine doses available. The use of an adjuvant may also be useful for overcoming the potential weak immunogenicity of the antigen in specific subjects such as in a naïve or immuno-compromised population. By way of examples, may be cited influenza viruses adjuvanted with aluminium salt, such as aluminium hydroxide or aluminium phosphate, or with oil-in-water emulsion. A sub-unit influenza vaccine adjuvanted with the oil-in-water emulsion MF59 is commercially available.

A classical assay for standardizing antigen content of influenza vaccines is the single radial immunodiffusion (SRID) assay (J. M. Wood et al.: An improved single radial immunodiffusion technique for the assay of influenza haemagglutinin antigen: adaptation for potency determination of inactivated whole virus and subunit vaccines. J. Biol. Stand. 5 (1977) 237-247; J. M. Wood et al., International collaborative study of single radial diffusion and immunoelectrophoresis techniques for the assay of haemagglutinin antigen of influenza virus. J. Biol. Stand. 9 (1981) 317-330), which was recommended by the WHO in 1978 to replace tests based on agglutination of erythrocytes. The assay is based on the immunodiffusion of influenza antigens, such as hemagglutinin (HA) antigen, into an agarose gel containing specific anti-HA serum, during which antigen/antibody complexes will be formed within the gel. HA antigen diffuses radially from the wells and reacts with specific antibodies, producing a zone of opalescence in the gel, typically in the form of a ring. The area of the reaction zone surrounding antigen-containing wells is an estimate of the quantity of antigen added to the well. Upon gel staining, the surface of these rings is measured, and the antigen content of a virus preparation of a certain subtype is calculated by using a calibration curve obtained with an antigen reference batch of this subtype with a known HA content.

However, such an assay may not be suitable for any type of influenza preparations or compositions, in particular, for adjuvanted preparations, as the presence of adjuvant may interfere with the normal test.

Therefore, there is a need to provide improvements to the SRID assay, so as to broaden its applicability and, in particular, to make it suitable for adjuvanted preparations or compositions, such as adjuvanted vaccines.

WO 2009/081172 discloses a modified influenza SRID assay protocol for an adjuvant-adsorbed antigen, in particular, for aluminium salt-adjuvanted vaccines, which includes an additional step in which the antigen is desorbed from the adjuvant prior to diffusion.

Therefore, there is still a need to provide for a modified SRID assay, in particular, suitable for assessing adjuvanted vaccines, which is easy and fast to implement, and applicable for identifying and/or quantifying antigens, such as HA, in any type of virus preparation, whether adjuvanted or not, including final vaccine formulations.

SUMMARY OF THE INVENTION

Accordingly, in a first aspect of the present invention, there is provided a method for performing an immunodiffusion assay comprising at least the following steps of:
  (a) preparing one or more test samples comprising an influenza virus antigen,
  (b) treating the test samples with at least 5% (w/v) detergent,
  (c) applying the treated samples to a gel containing an antibody specific to the influenza virus antigen, and
  (d) allowing the samples to diffuse into the gel.

In a second aspect, there is provided a method for quantitating the HA concentration of a vaccine comprising an influenza virus antigen which comprises at least the following steps of:
  (i) treating the vaccine, or a sample thereof, with at least 5% (w/v) of a detergent,
  (ii) treating reference samples comprising an influenza virus antigen of a known concentration with at least 5% (w/v) of a detergent,
  (iii) applying the treated vaccine, or a sample thereof, and the treated reference samples to a gel containing an antibody specific to the influenza antigen,
  (iv) allowing the samples to diffuse into the gel,
  (v) determining a dimension of precipitation rings in the gel formed by the vaccine, or a sample thereof, and a dimension of precipitation rings formed by the reference samples, and
  (vi) comparing together the dimensions determined in step (v) and using the results of the comparison to calculate the HA concentration in the vaccine, or a sample thereof, applied in step (iii).

DETAILED DESCRIPTION

The present invention relates to an immunodiffusion method for identifying an antigen of interest, such as a viral antigen, and/or determining the concentration of the antigen of interest within a preparation or a composition, such as a vaccine. In particular, the method of the invention provides a modified SRID assay which is not only suitable for non-adjuvanted virus preparations, but, especially, also for adjuvanted preparations, in particular, influenza vaccines adjuvanted with an oil-in-water emulsion.

The inventors, surprisingly, observed that an adjuvant, in particular, an oil-in-water emulsion, when present in a sample comprising a viral antigen, such as an influenza antigen, has a significant impact on the diffusion of the antigen during the SRID assay. The resulting diffusion ring is of an unusual type. Indeed, when compared to non-adjuvanted samples, the samples comprising an adjuvant, as processed through a SRID assay, resulted in a diffusion ring whose aspect was much darker and more diffuse, making the ring delimitation more blurred. They noticed that such a different aspect of the rings had an impact on the antigen quantification results obtained by the SRID assay. They observed that in the presence of the adjuvant, the results displayed a high variability and a lower antigen concentration, as compared to the results obtained with similar compositions which were not adjuvanted. Therefore, using the classical SRID assay used in the art for assessing the HA content of adjuvanted samples comprising an influenza antigen leads to an erroneous measurement of that content, as it is underestimated. Both the variability of the assay and the underestimation of the antigen concentration, which may lead to vaccine formulations with a miscalculated amount of antigen, have dramatic consequences, for instance, on the vaccines consistency and efficacy. Such drawbacks are unacceptable in the field of vaccine production.

The method according to the present invention provides a solution for overcoming these drawbacks and provides a robust, accurate and reliable method for identifying an antigen and/or determining the amount of the antigen, such as an influenza antigen, in virus preparations including vaccines. This method presents the advantage of being suitable for both adjuvanted and non-adjuvanted virus preparations. As a consequence, it is possible to test in parallel both adjuvanted and non-adjuvanted virus preparations with the method according to the invention, without requiring, thus, to employ two distinct methods. It is also a simple and easy method to implement.

The method of the present invention is used to identify an antigen of interest and/or determine the concentration of an antigen of interest, in particular, an influenza antigen, such as, for instance, hemagglutinin (HA).

The classical SRID assay was, originally, designed by Wood et al. (An improved single radial immunodiffusion technique for the assay of influenza haemagglutinin antigen: adaptation for potency determination of inactivated whole virus and subunit vaccines. J. Biol. Stand. 5 (1977) 237-247; International collaborative study of single radial diffusion and immunoelectrophoresis techniques for the assay of haemagglutinin antigen of influenza virus. J. Biol. Stand. 9 (1981) 317-330). This assay is now routinely used as a standard method for measuring the concentration of an influenza virus antigen, such as HA, within a composition, such as a vaccine. Many different vaccine manufacturing companies use the SRID assay for measuring the HA content of their influenza vaccines. This classical assay, typically, involves treating test samples comprising HA with a low concentration of detergent, usually 1% (w/v), before loading them in preformed wells on gel impregnated with specific anti-HA antibodies and letting the diffusion of the antigen into the gel occur (for instance, see WO 2009/000433, US 20090092620 and EP2014279). Typical detergents are zwitterionic detergents, such as Zwittergent. While WO 2009/081172 discloses higher doses of detergent, up to 8% (w/v), this higher dose is used and has only been shown to work, in combination with exogenously added salts, in particular, phosphate salts.

The method according to the invention, which is also called modified SRID in the rest of the specification, uses a concentration of detergent at least 5 times higher than the 1% (w/v) concentration used in the art. In particular, the concentration of detergent is at least 5% (w/v), suitably at least 8% (w/v), suitably at least 10% (w/v), suitably at least 15% (w/v) and suitably at least 20% (w/v). The method of the present invention has been shown to work with these concentrations of detergent, even in the absence of exogenously added salts. Detergents suitable for the method of the invention are similar to the detergents generally employed for the classical SRID assay. They may be ionic, such as sodium sarcosyl sulphate, or non-ionic, such as Triton X-100™, Nonidet P-40™, or Tween 80™. Non-ionic detergents include zwitterionic detergents. Zwitterionic detergents, including betaines, such as Empigen™, and sulfo-betains, such as zwittergents are particularly suitable for use in the modified SRID assay of the invention. In particular, the above zwitterionic detergents are suitably used when the antigen of interest whose concentration needs to be determined is an influenza virus antigen, such as HA. In one embodiment, the detergent used is a zwittergent, in particular, Zwittergent 3-14™ (n-Tetradecyl-N,N-dimethyl-3-ammonio-1-propanesulfonate) or Zwittergent 3-12™ (N-dodecyl-N,N-dimethyl-3-ammonio-1-propanesulfonate). In an alternative embodiment, the detergent is Empigen™. In one embodiment, the detergent concentration used for treating test samples and/or reference samples in the method of the invention, is suitably at least 5% (w/v), suitably at least 8% (w/v), suitably at least 10% (w/v), suitably at least 15%, and even 20% (w/v). In a particular embodiment, test samples and/or reference samples in the method of the invention are treated with more than 8% of detergent.

In the sense of the present invention, "treating a sample with a detergent" means that a detergent is added to the sample. The detergent may be left incubated. Suitably, the incubation time is at least 1 minute, suitably at least 5 minutes, suitably at least 10 min, suitably at least 20 min, and suitably at least 30 min. Typically, the incubation occurs under stirring, suitably, at room temperature.

Apart from the detergent percentage, the modified SRID assay may be performed in the same conditions as the conditions used when proceeding to a classical SRID assay. In particular, when used for measuring the antigen concentration within an adjuvanted sample, the method of the invention does not require a prior step of desorbing the antigen from the adjuvant.

For instance, the gels used in the modified SRID assay as disclosed therein are the same as the ones used for the classical SRID assay. They are suitably made of agar or agarose, although any other suitable materials may be used so long as they support radial diffusion of antigens and the precipitation of antigen/antibody complexes. They usually contain predefined circular wells into which samples are loaded. The contents of the wells then diffuse radially into the gel. A gel used in SRID assay, whether classical or modified, will typically include multiple wells for receiving samples and permitting parallel analysis. Accordingly, multiple samples of the same material, whether test samples or reference samples, can be tested in a single assay, usually at different sample dilutions.

The gels contain antibody specific to the antigen of interest at a concentration which allows the formation of immune complexes at a suitable distance from the centre of diffusion for a target antigen concentration. The antibody is present at a substantially uniform concentration, which may or may not be known. Preparation of such gels is known in the art. Antibody may be monoclonal or polyclonal. Suitably, the antibodies specific to the antigen of interest used for impregnating the gel are polyclonal.

According to one embodiment of the invention, the gel contains an antibody which is used to determine the concentration of an antigen of interest within a sample, for instance, the gel contains an anti-HA antibody used for measuring the concentration of a sample comprising an HA antigen from influenza virus.

In both the modified and the classical SRID assay, the result of the assay is the formation of a reaction zone in the gel between antigens diffusing from the wells they were loaded in and specific antibodies comprised in the gel. When wells are circular, the reaction zone is of a ring shape. The ring has an internal and an external diameter. The external diameter, or the surface delimited by the external demarcation of the ring, is proportional to the concentration of the antigen present within the well. Quantification of the antigen of interest may, thus, be obtained by comparing the dimension (diameter and/or surface) of the rings obtained after loading a well with a known concentration of a reference antigen. Diameters can be measured in two directions at right angle to each other. Alternatively, quantification may be obtained by comparing the respective surface measures of the rings. The measurement can be operated manually, i.e. by visual inspection using rulers or grids positioned directly above the rings. Alternatively, pictures of the plates displaying diffusion rings can be taken, or a live image can be captured by a camera linked to a computer. An on-screen ruler may then be used for measuring the rings, whether from a picture or from the live image. Alternatively, the measurement can be operated semi-automatically, i.e. an integrated software may provide a computer tool which allows to select or demarcate the rings surface, whether on pictures or on a live image. As a non-limiting example of a suitable device allowing such a measurement may be cited the KS400 device from Carl Zeiss. The software is then able to measure the surface, whether directly, for instance by measuring the pixel numbers comprised in the selected ring zone, or through the measure of the diameter in two right-angle directions. Alternatively, the measurement can be operated automatically. An example of an automatic measurement is described in WO 2005/033965. In one embodiment of the invention, diffusion ring dimensions are measured semi-automatically.

In the context of the present invention, a "test sample" is to be understood as any preparation or any composition, such as a vaccine, comprising an antigen of interest whose concentration needs to be determined. Said test sample may optionally include an adjuvant, in particular, an oil-in-water emulsion. In one embodiment, the test sample comprises an antigen of interest, in particular, an influenza virus antigen, such as HA, optionally in combination with an adjuvant, such as, for instance, an oil-in-water emulsion.

In the sense of the present invention a "reference sample", is a sample comprising an antigen serving as a reference, called a reference antigen, in that the concentration of the antigen is known. Suitably, this antigen is of the same type as the antigen of interest. Reference samples comprising reference antigen of known concentration are used for calibration, allowing in particular to draw a standard curve. Suitably, reference samples and test samples are prepared and treated in a similar manner when being processed through the modified SRID assay of the present invention. In particular, when test samples comprise an adjuvant, reference samples are typically added with a similar adjuvant, suitably in the same proportion, prior to proceeding to the assay. In one embodiment of the invention, the reference samples are added with the same adjuvant as the one present in the test samples (if any), suitably an oil-in-water emulsion.

The dimension (diameter and/or surface) of the precipitation ring determined after the diffusion of the test sample is compared to the dimension (diameter and/or surface) of the ring determined after diffusion of the reference sample. Typically, different dilutions of the reference samples are prepared and loaded on a gel, so as to obtain different ring dimensions (diameter or surface) corresponding to the concentrations of the different dilutions, allowing to draw the standard curve. By comparing the values of the ring dimension obtained for test samples to the values obtained for the reference samples, the concentration of the antigen of interest present within the test sample can be calculated. For example, the concentration can be calculated according to standard slope-ratio assay methods (Finney, D. J. (1952). Statistical Methods in Biological Assay. London: Griffin, Quoted in: Wood, J M, et al (1977). J. Biol. Standard. 5, 237-247). Accordingly, in one embodiment, the method of the present invention comprises the further step of (e) determining a dimension of precipitation rings formed in a gel by the test samples previously treated with a detergent, as described above, and applied on a gel comprising appropriate antibodies. In a further embodiment, the method of the present invention comprises the further step of (f) determining a dimension of precipitation rings formed in a gel by the reference samples previously treated with a detergent, as described above, and applied on a gel comprising appropriate antibodies. In a still further embodiment, the method of the present invention comprises the further step of (g) comparing the dimension determined in step (e) with the dimension determined in step (f) and using the results of the comparison to calculate the antigen concentration in test samples.

Reference antigens may be any antigen, which is similar to the antigen of interest and whose concentration is known, which concentration was determined according to any protein assay which is reliable, reproducible and free from interference by chemicals which may be present in the samples. As a non-limiting illustrative example, if measuring the antigen concentration within a vaccine formulation, optionally comprising an adjuvant, the reference antigen may be the antigen bulk which was obtained at the end of the production process, before the formulation step, for example before being formulated with an adjuvant. If the antigen is an influenza virus antigen, such as HA, the antigen concentration in the bulk is suitably measured by classical SRID assay. This type of reference antigens is particularly suitable when the method of the present invention is used to monitor vaccine stability, such as adjuvanted vaccines, as described below. Alternatively, reference antigens may be purified antigens provided by WHO (World Health Organisation) certified institutes, such as NIBSC (National Institute for Biologicals Standards and Control), whose concentration is known.

The determination of the antigen concentration, and thus, the content, within a test sample by the method according to the invention is suitable for calculating the exact amount which needs to be included in a final vaccine formulation. Alternatively, determining the antigen concentration or content according to the method of the invention is, suitably, used for examining the shelf life (i.e. stability) of a vaccine, whether adjuvanted or not, after it was produced and formulated. Therefore, the method of the invention for quantitating the antigen concentration or content within a composition, optionally, adjuvanted may have a broad application, in particular, in quality assay and quality control fields.

According to one embodiment, the method of the invention is used to monitor the stability of an antigen within a test sample, such as a vaccine, in particular a vaccine comprising an influenza virus antigen, optionally further comprising an adjuvant, such as an oil-in-water emulsion. For instance, the method of the invention can be used for quantitating the antigen concentration or content, such as HA, within a test sample, in particular, within a vaccine, after said sample, or vaccine, has been stored for a certain period of time after its formulation, such as 7 days, 14 days, 30 days, one month, or a few months, such as 6, 9, 12 or 18 months, at different temperatures, such as 4° C., room temperature, 30° C. or 37° C. The method of the invention is suitably used for quantitating the HA content within an influenza virus vaccine, optionally formulated with an adjuvant comprising an oil-in-water emulsion, which vaccine has been stored for a period of time selected from the group consisting of: 7 days, 14 days, 30 days, 1 month, 6 months and 18 months at the temperature selected from the group consisting of: 4° C., room temperature, 30° C. and 37° C.

The "test samples" suitably processed via the method of the present invention can contain any of a variety of antigens, in particular, bacterial antigens or viral antigens. Suitable bacterial antigens are, for instance, *H. influenzae* antigens, or tetanus antigens. By way of examples illustrating viral antigens, may be cited polio virus, rabies virus, or influenza virus.

A "test sample" which can be analyzed according to the method of the invention is suitably an influenza virus vaccine, which may have been produced according to any known methods, such as produced on eggs or propagated on cell culture. Suitable cell types supporting influenza virus replication and propagation are mammalian cell lines, such as, but not restricted to, MDCK, Vero, or PER.C6 cell lines. Alternatively to mammalian cell lines, avian cells are suitably used for replicating and propagating influenza virus, including chicken embryo fibroblasts, or cell lines derived from ducks, such as EB66® cells. The influenza vaccines currently available are generally based either on live virus or inactivated virus. The method of the invention can be used for analysing the antigen content of any type of influenza vaccine, in particular, of inactivated influenza vaccines, which may be based on whole virions, split viruses or purified surface antigens, such as in a subunit vaccine. Methods of viral inactivation are known in the art. Inactivation may occur by using at least one or more chemical agents, such as beta-propiolactone, or formaldehyde, as well as physical means, such as UV irradiation. Methods of splitting viruses, such as influenza viruses, are well known in the art (WO02/28422). Splitting of the virus is carried out by disrupting or fragmenting whole virus whether infectious (wild-type or attenuated) or non-infectious (inactivated) with a disrupting concentration of a splitting agent. Splitting agents generally include agents capable of breaking up and dissolving lipid membranes. Traditionally, split influenza virus was produced using a solvent/detergent treatment, such as tri-n-butyl phosphate, or diethylether in combination with Tween™ (known as "Tween-ether" splitting) and this process is still used in some production facilities. Other splitting agents now employed include detergents or proteolytic enzymes or bile salts, for example sodium deoxycholate. Detergents that can be used as splitting agents include cationic detergents e.g. cetyl trimethyl ammonium bromide (CTAB), other ionic detergents, e.g. sodium lauryl sulphate (SLS), taurodeoxycholate, or non-ionic detergents such as Tween™ or Triton X-100™, or combination of any two or more detergents. In one embodiment, the method of the present invention uses test samples comprising influenza viruses which were inactivated and/or split, which viruses were produced on eggs. In an alternative embodiment, the method of the present invention uses test samples comprising influenza viruses which were inactivated and/or split, which viruses were produced on cell culture, in particular, on avian cells, such as on EB66® cells.

Test samples, in addition to antigen and/or adjuvants may also include other pharmaceutical excipients, such as, but not restricted to polysorbate 80 (Tween 80™), octoxynol 10 (Triton X-100™), alpha-tocopheryl hydrogen succinate, sodium chloride, disodium hydrogen phosphate, potassium dihydrogen phosphate, potassium chloride, and/or water for injection.

The method according to the invention is suitable for measuring a wide range of concentrations of antigen. Accordingly, the method is applicable to test samples comprising a wide range of HA content, from 1-60 µg per dose or even higher. For instance, the method is suitable for measuring the HA amount present in an influenza virus trivalent vaccine, wherein each strain is usually present at an amount of 15 µg in a volume ranging from 250 µl to 750 µl, i.e. at a concentration varying from 20 µg HA/ml to 60 µg HA /ml per strain. The method of the invention is also suitable for measuring HA content present in test samples comprising a low amount of HA, i.e. preparations where the expected HA concentration is below 20 µg/ml per strain, in particular, below 15 µg/ml per strain, more particularly, below 10 µg/ml per strain. This may be the case for pandemic vaccines or paediatric vaccines. These low antigen doses may be combined with the presence of an adjuvant, such as an oil-in-water emulsion, to help boost the immune response to a lower antigen dose or to contribute to the antigen-sparing approaches. For instance, the method of the invention is applicable to a monovalent influenza vaccine including, for instance, a pandemic strain, wherein the HA content is between 1-10 µg HA per dose, i.e. a concentration ranging from 2-20 µg HA/ml for a classical 0.5 ml dose. Suitably, the HA concentration per strain in the vaccine is between 1-20 µg/ml, more suitably, between 5-10 µg/ml. Suitably, the HA concentration per strain in the preparation is about 15 µg/ml, 7.5 µg/ml, 3.8 µg/ml or lower. Therefore, if desired, the test samples, such as vaccines, may be diluted so as to lower the antigen concentration, before treating the samples with a detergent according to the method of the invention and loading the treated samples onto the gel.

In particular, the inventors observed that if diluting adjuvanted samples, so as to lower the expected concentration down to less than 20 µg of antigen/ml, the antigen concentration results obtained according to the method of the invention is further improved. Accordingly, in one embodiment, the method according to the invention involves a step of diluting the test samples before treating it with a detergent. In particular, after the dilution the concentration is less than 20 µg of antigen/ml, more particularly, ranges from 5-20 µg/ml, such as 7.5 µg/ml. The prior dilution is suitably performed when the method of the invention is used for monitoring the stability of a test sample, such as a vaccine, optionally comprising an adjuvant, such as an oil-in-water emulsion, as described above. Typically, when monitoring the stability of a vaccine, the concentration of the antigen is initially determined at the end of the antigen bulk production, i.e. before being formulated, in particular, before being combined with an adjuvant. As described earlier, said determination may be accomplished by using the classical SRID assay. Accordingly, the initial concentration serves as the expected concentration in the subsequent stability tests. The subsequent concentrations determined after specific storage conditions of the vaccine will be normalised against the expected concentration, accounting thus for the stability of the antigen in the vaccine.

In one embodiment, the invention provides a method for performing an immunodiffusion assay comprising at least the following steps of:
- (A) Preparing one or more test samples comprising an influenza virus antigen
- (B) Diluting test samples so as to obtain an expected concentration of less than 20 μg antigen/ml, in particular, ranging from 5 to 20 μg/ml, suitably 7.5 μg/ml,
- (C) Applying the samples to a gel containing an antibody specific to the influenza antigen, and
- (D) Allowing the samples to diffuse into the gel.

This method is suitably used for monitoring the stability of the test samples.

As the production of a vaccine comprises numerous steps, in particular, various purification steps of the antigen of interest, a "test sample" in the sense of the present invention also encompasses any composition comprising an antigen of interest which is an intermediate in the vaccine production process, as opposed to the final vaccine formulation.

A vaccine may be formulated in various forms. For instance, it can be in a lyophilized form or in a liquid formulation ready to use. The method of the invention may be applicable for determining the antigen concentration of both types of formulation. However, if it is lyophilized, it first needs to be reconstituted in a liquid solution. For instance, the vaccine to be tested, which comprises the antigen of interest, may be in a lyophilized form which is reconstituted, prior to use, in an adjuvant solution, if the vaccine is to be adjuvanted, or in any physiologically compatible solution, if the vaccine is to be non-adjuvanted. As a consequence, the test sample, in particular a vaccine, may be presented in the form of one or more vials, such as two vials. The two-vial presentation, for example, provides one vial comprising the antigen of interest, whether in a lyophilized form or in a liquid form, and the second vial comprises an adjuvant in a liquid form, for example, an oil-in-water emulsion. The method of the invention is applicable to any kind of vaccine presentation and may also be used for measuring the antigen content of a vaccine which has been reconstituted.

The test samples, such as vaccines, whether or not adjuvanted, which need to be tested for their antigen concentration and content by the method of the invention may be monovalent, or multivalent. In particular, the multivalent test sample is a trivalent vaccine or a quadrivalent vaccine. In one embodiment, the vaccine to be tested is adjuvanted and comprises influenza antigens of one, three or four distinct strains. In a specific embodiment the influenza vaccine is a trivalent vaccine. In a distinct embodiment, the vaccine is quadrivalent. In an alternative embodiment, the influenza vaccine is a monovalent vaccine comprising one influenza strain, in particular, of a pandemic potential.

Influenza viruses are enveloped negative-sense RNA viruses with a segmented genome belonging to the Orthomyxoviridae family. They are classified on the basis of their core proteins into three distinct types: A, B, and C [Cox N J, Fukuda K. Influenza. *Infect. Dis. Clin. North Am.* 1998;12: 27-38]. Influenza A viruses can infect a range of mammalian and avian species, whereas types B and C are essentially restricted to human beings. Influenza A and B viruses are mainly responsible for human disease with type A being the most pathogenic. The main antigenic determinants of influenza A and B viruses are two surface glycoproteins: neuraminidase (NA) and hemagglutinin (HA), both capable of eliciting immune response in human beings. HA is involved in receptor binding and membrane fusion. NA facilitates cleavage of virus progeny from infected cells, prevents viral aggregation, and aids movement through the mucosal respiratory-tract epithelium. Virus strains are classified according to host species of origin, geographical site, year of isolation, serial number, and, for influenza A, by serological properties of HA and NA subtypes. Sixteen HA subtypes (H1-H16) and nine NA subtypes (N1-N9) have been identified for influenza A viruses [Webster R G et al. Evolution and ecology of influenza A viruses. *Microbiol. Rev.* 1992;56:152-179; Fouchier R A et al. Characterization of a Novel Influenza A Virus Hemagglutinin Subtype (H16) Obtained from Black-Headed Gulls. *J. Virol.* 2005;79:2814-2822). Viruses containing all HA and NA subtypes have been recovered from aquatic birds, but only three HA subtypes (H1, H2, and H3) and two NA subtypes (N1 and N2) have established stable lineages in the human population since 1918. Only one subtype of HA and one of NA are recognised for influenza B viruses.

Influenza antigens may be derived from interpandemic (annual or seasonal) influenza strains. Alternatively, influenza antigens may be derived from strains with the potential to cause a pandemic outbreak (i.e., influenza strains with new hemagglutinin compared to hemagglutinin in currently circulating strains, or influenza strains which are pathogenic in avian subjects and have the potential to be transmitted horizontally in the human population, or influenza strains which are pathogenic to humans). Depending on the particular season and on the nature of the antigen included in the vaccine, the influenza antigens may be derived from one or more of the following hemagglutinin subtypes: H1, H2, H3, H4, H5, H6, H7, H8, H9, H10, H11, H12, H13, H14, H15 or H16. Suitably the influenza antigens will be selected from the group of: H1, H2, H3, H5, H7 and H9.

Optionally, test samples and/or reference samples can include an adjuvant, in particular an oil-in-water emulsion. Suitably, the method of the present invention allows to measure antigen concentration in test samples, such as vaccines, comprising an oil-in-water emulsion, optionally comprising other immunostimulants. In particular, the oil phase of the emulsion system comprises a metabolisable oil. The meaning of the term metabolisable oil is well known in the art. Metabolisable can be defined as 'being capable of being transformed by metabolism' (Dorland's Illustrated Medical Dictionary, W.B. Sanders Company, 25th edition (1974)). The oil may be any vegetable oil, fish oil, animal oil or synthetic oil, which is not toxic to the recipient and is capable of being transformed by metabolism. Nuts, seeds, and grains are common sources of vegetable oils. Synthetic oils are also part of this invention and can include commercially available oils such as NEOBEE® and others. A particularly suitable metabolisable oil is squalene. Squalene (2,6,10,15,19,23-Hexamethyl-2,6,10,14,18,22-tetracosahexaene) is an unsaturated oil which is found in large quantities in shark-liver oil, and in lower quantities in olive oil, wheat germ oil, rice bran oil, and yeast, and is a particularly suitable oil for use in the oil-in-water emulsion. Squalene is a metabolisable oil by virtue of the fact that it is an intermediate in the biosynthesis of cholesterol (Merck index, 10th Edition, entry no.8619). In one embodiment of the invention, the metabolisable oil is present in test samples and/or reference samples in an amount of 0.5% to 10% (v/v) of the total volume of the sample.

The oil-in-water emulsion further comprises an emulsifying agent. The emulsifying agent may suitably be polyoxyethylene sorbitan monooleate, such as Tween 80™ or Polysorbate™. Said emulsifying agent is suitably present in test samples and reference samples in an amount of 0.125 to 4% (v/v) of the total volume of the sample.

The oil-in-water emulsion optionally comprise a tocol. Tocols are well known in the art and are described in EP0382271. A suitable tocol is tocopherol, in particular alpha-tocopherol or a derivative thereof such as alpha-tocopherol succinate (also known as vitamin E succinate). Said tocol is suitably present in test samples and/or reference samples in an amount 0.25% to 10% (v/v) of the total volume of the sample or vaccine.

The adjuvant composition, in particular, the oil-in-water emulsion, may further comprise a Toll like receptor (TLR) 4 agonist. By "TLR4 agonist" it is meant a component which is capable of causing a signalling response through a TLR4 signalling pathway, either as a direct ligand or indirectly through generation of endogenous or exogenous ligand (Sabroe et al, JI 2003 p 1630-6). The TLR 4 may be a lipid A derivative, particularly monophosphoryl lipid A or more particularly 3 Deacylated monophoshoryl lipid A (3D -MPL).

Suitably the oil-in-water emulsion comprises a metabolisable oil, such as squalene, a tocol, such as alpha-tocopherol, and an emulsifying agent, such as Tween 80™. Accordingly, in one embodiment of the invention, test samples and/or reference samples comprise squalene, alpha-tocopherol and Tween 80™, optionally, in combination with 3D-MPL.

3D-MPL is available under the trademark MPL® by GlaxoSmithKline Biologicals North America and primarily promotes CD4+ T cell responses with an IFN-g (Th1) phenotype. It can be produced according to the methods disclosed in GB 2 220 211 A. Chemically it is a mixture of 3-deacylated monophosphoryl lipid A with 3, 4, 5 or 6 acylated chains. In particular, in the adjuvant compositions of the present invention small particle 3D-MPL is used. Small particle 3D-MPL has a particle size such that it may be sterile-filtered through a 0.22 μm filter. Such preparations are described in International Patent Application No. WO 94/21292. Synthetic derivatives of lipid A are known and thought to be TLR 4 agonists including, but not limited to:

OM174 (2-deoxy-6-o-[2-deoxy-2-[(R)-3-dodecanoyloxytetra-decanoylamino]-4-o-phosphono-β-D-glucopyranosyl]-2-[(R)-3-hydroxytetradecanoylamino]-α-D-glucopyranosyldihydrogenphosphate), (WO 95/14026)

OM 294 DP (3S, 9 R)—3-[(R)-dodecanoyloxytetradecanoylamino]-4-oxo-5-aza-9(R)-[(R)-3-hydroxytetradecanoylamino]decan-1,10-diol,1,10-bis(dihydrogenophosphate) (WO99/64301 and WO 00/0462)

OM 197 MP-Ac DP (3S-, 9R)—3-[(R) -dodecanoyloxytetradecanoylamino]-4-oxo-5-aza-9-[(R)-3-hydroxytetradecanoylamino]decan-1,10-diol,1-dihydrogenophosphate 10-(6-aminohexanoate) (WO 01/46127)

Other TLR4 ligands which may be used are alkyl Glucosaminide phosphates (AGPs) such as those disclosed in WO9850399 or U.S. Pat. No. 6,303,347 (processes for preparation of AGPs are also disclosed), or pharmaceutically acceptable salts of AGPs as disclosed in U.S. Pat. No. 6,764, 840. Some AGPs are TLR4 agonists, and some are TLR4 antagonists. Both are thought to be useful as adjuvants. In addition, further suitable TLR-4 agonists are disclosed in US2003/0153532 and US2205/0164988.

The method of the invention for measuring the antigen concentration within an adjuvanted sample, such as a vaccine, is applicable to a wide range of adjuvant concentration within the vaccine. If considering an influenza vaccine comprising an oil-in-water emulsion, suitably said emulsion comprises 11 mg metabolisable oil (such as squalene) or below, for example between 0.5-11 mg, 0.5-10 mg or 0.5-9 mg 1-10 mg, 1-11 mg, 2-10 mg, 4-8 mg, or 4.5-5.5 mg, and 5 mg emulsifying agent (such as polyoxyethylene sorbitan monooleate) or below, for example between 0.1-5 mg, 0.2-5 mg, 0.3-5 mg, 0.4-5 mg, 0.5-4 mg, 1-2 mg or 2-3 mg per dose of the vaccine. Suitably tocol (e.g. alpha-tocopherol) where present is 12 mg or below, for example between 0.5-12 mg, 10-11 mg, 1-11 mg, 2-10 mg, 4-9 mg, or 5-7 mg per vaccine dose. Typically, influenza vaccine doses range from 0.25 ml to 1.5 ml, suitably, about 0.5 ml, suitably about 0.6 ml, suitably, about 0.7 ml, suitably, about 0.8 ml, suitably, about 0.9 ml or about 1 ml.

The invention will be further described by reference to the following, non-limiting, examples.

Example 1

Comparison of Using Detergent 1% Versus Detergent 10% in an SRID Assay for Analysing the HA Content of a Vaccine Which is Non-Adjuvanted or Formulated with an Adjuvant The influenza vaccine lot VFFLU04-14 was tested for its HA content according to the modified SRID assay of the invention, as compared to the use of the classical SRID assay of the prior art. It is a trivalent split virion, inactivated influenza vaccine consisting of three monovalent viral antigen bulks (prepared from the respective influenza strains A/New Caledonia H1N1, AM/yoming H3N2 and B/Jiangsu). After their production, the HA concentration of the three monovalent bulks was measured by using the classical SRID assay employing Zwittergent 3-14™ 1% (Calbiochem). Based on this concentration, 15 μg of each bulk was included in the 500 μl vaccine dose. Therefore, the expected HA concentration of any of the three strains within the dose is 30 μg HA/ml. This vaccine lot was, then, formulated in two different forms. It was either left non-adjuvanted (referred to as the Plain form) or adjuvanted with an oil-in-water emulsion comprising squalene, alpha-tocopherol, Tween 80™ and 3D-MPL (referred to as the OW form). The HA content for two of the strains (AM/yoming H3N2 and B/Jiangsu) of each formulation (Plain and OW) was analyzed according to the classical SRID assay (Zwittergent 3-14™ 1%) and the modified SRD assay of the present invention (Zwittergent 3-14™ 10%). HA reference antigens (referred to as Ref Ag) specific to each tested strain and of known concentrations (provided by NIBSC) were used as controls allowing to quantify the HA content of each tested strain in both types of vaccine formulations (Plain and OW). As an additional control to the experiment, monovalent bulks specific to each tested strain were also used (referred to as monobulks). As indicated above, at the end of their production and before being formulated as a vaccine lot, the HA concentration of each monobulk is always measured by the classical SRID assay (Zwittergent 3-14™ 1%). Therefore, as an internal control for the present experiment, the HA concentration of monobulks specific to each tested strain was recalculated along with the formulated vaccine VFFLU04-14 using both the classical and the modified SRID assay. Reference antigens, formulated vaccines and monobulks were incubated in the presence of Zwittergent 3-14™ 1% or Zwittergent 3-14™ 10% for 30 min under stirring at room temperature. They were, then, diluted according to the following scheme : 1/1 (undiluted), 3/4, 1/2, 1/4. All dilutions relating to the strain A Wyoming/H3N2 were loaded on wells in an agarose gel impregnated with an antiserum specific for that strain (provided by a WHO certified institute), while dilutions relating to the strain B Jiangsu were loaded on wells in an agarose gel impregnated with an antiserum specific for this strain (also provided by NIBSC). Gels were incubated for 24 hours at room temperature (20 to 25° C.) in a moist chamber, so as to allow the immunodiffusion to happen and the precipitation rings around the wells to form. After that, they were soaked overnight with NaCl solution and washed briefly in distilled water. The gel was then pressed and dried. When completely dry, the gels were stained in a Coomassie Brillant Blue solution for 10 minutes and destained twice in a mixture of methanol and acetic acid until clearly defined stained zones become visible. After drying the stained gels, pictures were taken and measurements of the surface of the precipitation rings were performed using the KS400 device (Carl Zeiss). The surface is expressed in arbitrary units. Said measurements, for each dilution, are presented in Table 1 (A Wyoming H3N2 strain) and Table 2 (B Jiangsu strain). The values represent a mean value, as each dilution was loaded in duplicates and three different measurements per dilution were performed.

TABLE 1

A/Wyoming/H3N2 - Surface values of the precipitation rings

| | | ANTIGEN DILUTIONS | | | |
|---|---|---|---|---|---|
| SAMPLE | Zwittergent (%) | 1/1 | 3/4 | 1/2 | 1/4 |
| Ref Ag | 1% | 137.2 | 125.5 | 109.5 | 98 |
| A/W/H3N2 | 10% | 131.3 | 123 | 108.6 | 101 |
| Vaccine | Plain—1% | 128.5 | 119.2 | 109.3 | 98 |
| VFFLU04-14 | Plain—10% | 126.5 | 118.2 | 107.3 | 97.6 |
| | OW—1% | 103.6 | 100.3 | 97.8 | 94.8 |
| | OW—10% | 119.5 | 111.7 | 103.8 | 98.3 |
| Monobulk | 1% | 129.3 | 119.8 | 108.2 | 97 |
| A/W/H3N2 | 10% | 126.7 | 117.3 | 106.7 | 97.2 |

Zwittergent 3-14 ™ % are in w/v

TABLE 2

B Jiangsu - Surface values of the precipitation rings

| | | ANTIGEN DILUTIONS | | | |
|---|---|---|---|---|---|
| SAMPLE | Zwittergent % | 1/1 | 3/4 | 1/2 | 1/4 |
| Ref Ag | 1% | 128.8 | 117.1 | 107 | 97.1 |
| B/Jiangsu | 10% | 123.2 | 116.2 | 104.3 | 100.7 |
| Vaccine | Plain—1% | 125.8 | 116.6 | 107.5 | 96.8 |
| VFFLU04-14 | Plain—10% | 123.6 | 115.75 | 107.2 | 97.9 |
| | OW—1% | 102 | 98.9 | 97.6 | 94.25 |
| | OW—10% | 119.9 | 113.7 | 105.1 | 96.5 |
| Monobulk | 1% | 126.7 | 118 | 107.3 | 96.7 |
| B/Jiangsu | 10% | 125.8 | 117.7 | 106.7 | 97.6 |

Zwittergent 3-14 ™ % are in w/v

Surface values were used to construct dose-response curves of antigen dilutions against the surface. The concentrations of the samples were then calculated according to standard slope-ratio assay methods (Finney, D. J. (1952). Statistical Methods in Biological Assay. London: Griffin, Quoted in: Wood, J M, et al (1977). J. Biol. Standard. 5, 237-247). Concentration results for the A/Wyoming/H3N2 and the B/Jiangsu strains are presented in Table 3 and Table 4, respectively. The values of the "expected µg HA/ml" columns result from the concentration of the monobulks before formulation into the vaccine, measured by using the classical SRID assay (Zwittergent 3-14™ 1%). Based on this concentration value, 15 µg of each monobulk was included in a 500 µl dose, so that the expected HA concentration value within the vaccine VFFLU04-14 is 30 µg/ml. HA recovery percentages are to be compared to the control value of 100% corresponding to the HA expected concentration.

TABLE 3

A/Wyoming/H3N2 - Concentration values

| SAMPLE | Zwittergent % | µg HA/ml | Expected µg HA/ml | HA Recovery (%) |
|---|---|---|---|---|
| Vaccine | Plain—1% | 29 | 30 | 96 |
| VFFLU04-14 | Plain—10% | 31 | 30 | 103 |
| | OW—1% | 13 | 30 | 43 |
| | OW—10% | 24 | 30 | 80 |
| Monobulk | 1% | 196 | 237 | 83 |
| A/W/H3N2 | 10% | 203 | 237 | 86 |

Zwittergent 3-14 ™ % are in w/v

TABLE 4

B/Jiangsu - Concentration values

| SAMPLE | Zwittergent % | µg HA/ml | Expected µg HA/ml | HA Recovery (%) |
|---|---|---|---|---|
| Vaccine | Plain—1% | 33 | 30 | 106 |
| VFFLU04-14 | Plain—10% | 36 | 30 | 120 |
| | OW—1% | 13 | 30 | 43 |
| | OW—10% | 32 | 30 | 106 |
| Monobulk | 1% | 240 | 247 | 101 |
| B/Jiangsu | 10% | 268 | 247 | 108 |

Zwittergent 3-14 ™ % are in w/v

Results—Conclusions

Table 1 and Table 2, both displaying surface values of the precipitation rings, indicate that using Zwittergent 10%, as opposed to Zwittergent 1%, does not have any impact on the size of the rings formed by non-adjuvanted sample. Indeed, if considering the Ref Ag rows, surfaces values are similar, regardless of the Zwittergent concentration which was used. The same conclusion applies, if considering the Plain vaccine rows or the Monobulk rows. No difference in surface values is observed when using Zwittergent 10%, as compared to using Zwittergent 1%. This observation applies to both tested strains, i.e. A/Wyoming H3N2 (see Table 1) and B/Jiangsu (see Table 2).

If considering the Vaccine rows of Table 1 and Table 2, and if comparing the Plain formulation with the OW formulation while using Zwittergent 1%, the surface values obtained indicate that the presence of the adjuvant has a negative impact on the size of the precipitation ring. Indeed, values in the OW formulations are lower than the values in the Plain formulations (see dilutions 1/1 and 3/4 of Table 1 and Table 2, where ring sizes are from 15 to 20% smaller when the formulation is adjuvanted). The ring size-decrease phenomenon, when the vaccine formulation is adjuvanted, is becoming less visible when the samples are more diluted (see dilutions 1/2 and 1/4 of Table 1 and Table 2). In this experiment, the 1/1, 3/4, 1/2, and 1/4 dilutions of the vaccine lot VFFLU04-14 represent theoretical concentrations of 30, 22.5, 15 and 7.5 µg HA/ml, respectively. Therefore, the results presented here suggest that diluting adjuvanted samples prior to their testing by SRID assay may be advantageous, as at a lower concentration the negative impact of adjuvant on the size of the precipitation ring is attenuated.

If considering still the Vaccine rows of Table 1 and Table 2, and if comparing the OW formulation using Zwittergent 1%, with the OW formulation using Zwittergent 10%, the surface values are higher when using Zwittergent 10% and allows to achieve values similar to the ones obtained for Plain formulation, i.e. non-adjuvanted (see dilutions 1/1 and 1/2 of Table 1 and Table 2). These results indicate that using 10 times more Zwittergent when a formulation is adjuvanted allows to overcome the ring size defect which is observed when using only Zwittergent 1%.

Table 3 and Table 4, both displaying the quantified HA concentrations, as a result of the surface values measured in Table 1 and Table 2, indicate that when the adjuvant is present in the formulation (OW formulation), and if using Zwittergent 1%, the HA concentration is significantly lower, as compared to the concentration obtained when the formulation is non-adjuvanted (Plain formulation). This observation is applicable to both strains, A/Wyoming/H3N2 (Table 3) and B/Jiangsu (Table 4), where the HA concentration is, respectively, 2.2 and 2.5 times lower in the OW formulation, as compared to the Plain formulation, while using Zwittergent 1%.

When using Zwittergent 10%, the HA concentration in the OW formulation is increased by an approximate 2-fold factor, as compared to the concentration in the OW formulation when using Zwittergent 1%, achieving, thus, a concentration which is similar to the concentration obtained in non-adjuvanted formulations (Plain formulation). This observation is clearly confirmed and illustrated by the recovery HA values.

Table 3 and Table 4 also confirm that using 10% Zwittergent has no negative impact on the concentration results, as compared to using Zwittergent 1%. Indeed, both 1% and 10% give similar concentrations for Plain formulations or Monobulks.

Example 2

Using Detergent 10% in an SRID Assay for Analysing the HA Content of a Vaccine Formulated with an Adjuvant The influenza vaccine lot EFLAA004A was tested for its HA content according to the modified SRID assay of the invention. It is a quadrivalent influenza vaccine including the A/Brisbane/H1N1 strain. After its production, the HA concentration of the A/Brisbane/H1N1 monovalent bulk, or monobulk, was measured by using the classical SRID assay employing Zwittergent 3-14™ 1% (Calbiochem). This monobulk was included in the vaccine at the concentration of 30 µg/ml, which represents in this experiment the expected concentration. This vaccine lot was, then, formulated with an oil-in-water emulsion adjuvant comprising squalene, alpha-tocopherol, and Tween 80™ The HA content for the A/Brisbane/H1N1 strain was analyzed according to the modified SRD assay of the present invention (Zwittergent 3-14™ 10%). An HA reference antigen (referred to as Ref Ag) specific for this strain and of known concentration (provided by NIBSC) was used as a control allowing to quantify the HA content of this strain. As a an additional control to the experiment, a monovalent bulk of this strain obtained before formulation was also used (referred to as Monobulk). At the end of production and before being formulated as a vaccine lot, the HA concentration of each monobulk has been measured by the classical SRID assay (Zwittergent 3-14™ 1%). Therefore, as an internal control for the present experiment, the HA concentration of this monobulk was recalculated along with the adjuvanted vaccine EFLAA004A using the modified SRID assay. The reference antigen and the monobulk were, first, admixed with the same proportion of the same adjuvant composition as the ones used in the formulated EFLAA004A vaccine. The adjuvanted reference antigen, the adjuvanted vaccine and the adjuvanted monobulk were, then, incubated in the presence of Zwittergent 3-14™ 10% for 30 min under stirring. They were, then, diluted according to the following scheme: 1/1 (undiluted), 3/4, 1/2, 1/4. All dilutions were loaded on wells in an agarose gel impregnated with an antiserum specific for the A/Brisbane/H1N1 strain (provided by a WHO certified institute). The rest of the assay was performed as described in Example 1.

The surface values are presented in Table 5 and the concentration values in Table 6.

TABLE 5

A/Brisbane H1N1 - Surface values of the precipitation rings

| | | ANTIGEN DILUTIONS | | | |
|---|---|---|---|---|---|
| SAMPLE | Zwittergent (%) | 1/1 | 3/4 | 1/2 | 1/4 |
| Ref Antigen | 10% | 149.6 | 135.6 | 122.6 | 111.4 |
| Vaccine EFLAA004 | 10% | 148.8 | 137.2 | 123.9 | 103.2 |
| Monobulk A/H1N1 | 10% | 141.9 | 131.2 | 116.7 | 99.0 |

Zwittergent 3-14 ™ % is in w/v

TABLE 6

A/Brisbane H1N1 - Concentration values

| SAMPLE | Zwittergent % | µg HA/ml | Expected µg HA/ml | HA Recovery (%) |
|---|---|---|---|---|
| Vaccine EFLAA004 | 10% | 30.3 | 30 | 101 |
| Monobulk A/H1N1 | 10% | 689.2 | 790 | 87 |

Zwittergent 3-14 ™ % are in w/v

Results—Conclusions

Table 6 indicates that the HA concentration determined when using the modified SRID assay, i.e. Zwittergent 10%, on a vaccine lot adjuvanted with an oil-in-water emulsion gives similar results as the expected concentration. The expected concentration corresponds to the concentration measured before the monobulk was formulated with the adjuvant. Therefore, as no difference is observed between the two values, this indicates that using 10% of Zwittergent does not result in an underestimation of the HA concentration within an adjuvanted vaccine, as compared to the same non-adjuvanted vaccine.

General Conclusion

These results suggest that the modified SRID assay of the present invention, employing 10% of Zwittergent, provides an improved method for measuring the HA concentration in adjuvanted vaccines which is reliable and accurate. Furthermore, as concluded from the Example 1, this modified SRID assay does not have any impact on the measurement performed in non-adjuvanted vaccines, making this method suitable for both types of vaccine formulations, i.e. adjuvanted and non-adjuvanted.

Example 3

Dose Range Testing of Different Detergents for Analysing the HA Content of a Vaccine Formulated with an Adjuvant by SRID Assay The influenza vaccine lot DFLUA038AA was assessed for its HA content by SRID assay. It is a monovalent influenza vaccine including the A/California/H1N1 strain. After production, the HA concentration of the monovalent bulk, or monobulk, was measured by using the classical SRID assay employing Zwittergent 3-14™ 1%. When performing the assay, an HA reference antigen of a known concentration specific to this strain was used as the control to draw the standard curve (provided by NIBSC, X179). The monobulk was included in the vaccine at the concentration of 15 µg/ml which represents the expected concentration in these experiments. This vaccine lot was then formulated with an oil-in-water emulsion adjuvant comprising squalene, alpha-tocopherol, and Tween 80™. The HA content was analysed by SRID assay, testing (a) a dose range of Zwittergent 3-14™ : 1% (v/w), 5% (v/w), 10% (v/w), 15% (v/w), and 20% (v/w), as well as (b) distinct detergents, such as Empigen, Zwittergent 3-12™, and Triton-X 100™. An HA reference antigen (referred to as Ref Ag) of a known concentration and specific to the A/California/H1N1 strain (provided by NIBSC, X181) was used as the control allowing to draw the standard curve. The reference antigen was added with the same adjuvant as the one used in the formulated DFLUA038AA vaccine and in the same proportion. (i) In a first experiment, the adjuvanted reference antigen was added with Zwittergent 3-14™ 10% (v/w). Different samples of the adjuvanted vaccine were added, respectively, with 1% (v/w), 5% (v/w), 10% (v/w), 15% (v/w) and 20% (v/w) of Zwittergent 3-14™. (ii) In a second experiment, different adjuvanted reference antigen samples were added with Triton X-100™ 1% (v/w) and Triton X-100 ™ 3.6% (v/w). Different samples of the adjuvanted vaccine were added, respectively, with 1% (v/w) and 3.6% (v/w) of Triton X-100™. (iii) In a third experiment, different adjuvanted reference antigen samples were added, respectively, with Empigen™ 1% (v/w) and Empigen™ 10% (v/w). Different samples of the adjuvanted vaccine were added, respectively, with 1% (v/w) and 10% (v/w) of Empigen™. (iv) In a fourth experiment, the adjuvanted reference antigen and the adjuvanted vaccine were added with Zwittergent 3-12™ 10% (v/w). All the above adjuvanted reference antigen samples and the adjuvanted vaccine samples were incubated with the respective detergent for 30 min under stirring at room temperature. All of them were then diluted according to the scheme: 1/1 (undiluted), 3/4, 1/2, 1/4. All dilutions were loaded on wells in an agarose gel impregnated with an antiserum specific to the A/California/H1N1 strain. The rest of the assay was performed as described in Example 1.

The surface values of the precipitation rings obtained in the experiment (i) (dose range of Zwittergent 3-14™) are presented in Table 7. Concentration values calculated in experiments (i) (dose range of Zwittergent 3-14™), (ii) (Triton X-100), (iii) (Empigen) and (iv) (Zwittergent 3-12™) are presented in Table 8.

TABLE 7

A/California H1N1 - Surface values of the precipitation rings

| SAMPLE | Zwittergent (%) | ANTIGEN DILUTIONS | | | |
|---|---|---|---|---|---|
| | | 1/1 | 3/4 | 1/2 | 1/4 |
| Ref Antigen A/H1N1 | 10% | 122.3 | 116.5 | 110.0 | 96.8 |
| Vaccine DFLUA038AA | 1% | 100.5 | 100.8 | 95.0 | 95.5 |
| Vaccine DFLUA038AA | 5% | 113.8 | 109.8 | 105.2 | 94.2 |
| Vaccine DFLUA038AA | 10% | 116.8 | 109.7 | 105.5 | 97.5 |

TABLE 7-continued

A/California H1N1 - Surface values of the precipitation rings

| SAMPLE | Zwittergent (%) | ANTIGEN DILUTIONS | | | |
|---|---|---|---|---|---|
| | | 1/1 | 3/4 | 1/2 | 1/4 |
| Vaccine DFLUA038AA | 15% | 117.8 | 112.0 | 105.5 | 97.5 |
| Vaccine DFLUA038AA | 20% | 117.2 | 111.7 | 106.7 | 94.0 |

Zwittergent % are in w/v

TABLE 8

A/California H1N1 - Concentration values

| SAMPLE | Detergent (%) | µg HA/ml | Expected µg HA/ml | HA recovery (%) | HA recovery (%) ** |
|---|---|---|---|---|---|
| Vaccine DFLUA038AA | Zwitt. 3-14™ 1% | 12.5 | 15 | 83 | 64 |
| Vaccine DFLUA038AA | Zwitt. 3-14™ 5% | 19.5 | 15 | 130 | 100 |
| Vaccine DFLUA038AA | Zwitt. 3-14™ 10% | 19.5 | 15 | 130 | 100 |
| Vaccine DFLUA038AA | Zwitt. 3-14™ 15% | 20.25 | 15 | 135 | 104 |
| Vaccine DFLUA038AA | Zwitt. 3-14™ 20% | 20.25 | 15 | 135 | 104 |
| Vaccine DFLUA038AA | Triton X-100™ 1% | * | 15 | * | * |
| Vaccine DFLUA038AA | Triton X-100™ 3.6% | * | 15 | * | * |
| Vaccine DFLUA038AA | Empigen™ 1% | * | 15 | * | * |
| Vaccine DFLUA038AA | Empigen™ 10% | 15.7 | 15 | 104 | 80 |
| Vaccine DFLUA038AA | Zwitt. 3-12™ 10% | 17 | 15 | 113 | 86 |

Detergent % are in w/v
* In these detergent conditions, no diffusion rings were obtained with reference antigens
** In this column, HA recoveries have been normalized against HA recovery obtained when using Zwittergent 3-14 ™ 10%

Results—Conclusions

Table 8 indicates that, amongst the Zwittergent 3-14™ conditions, only Zwittergent 3-14™ 1% (which is the percentage used in the art) resulted in an HA concentration which is lower than the expected concentration (HA recovery is 83%), confirming the observation previously made in Examples 1 and 2 that Zwittergent 3-14™ 1%, when used for assessing an adjuvanted vaccine, does not provide accurate results as it results in an underestimated HA concentration. On the contrary, when performing the SRID assay with Zwittergent 3-14™ 5%, 10%, 15% or 20%, the resulting HA concentration reaches the expected concentration (HA recoveries are 130% and 135%). The observation that the concentrations are higher than the expected concentration is explained by the fact that reference antigens during the initial classical SRID assay (Zwittergent 3-14™ 1%), which has allowed to include the A/California/H1N1 strain in the vaccine lot DFLUA038AA at the concentration of 15 µg HA/ml (expected concentration), and reference antigens during the subsequent modified SRID assay testing the different detergent conditions were not identical. Accordingly, in order to compare the ability of the different Zwittergent 3-14™ conditions to provide a measurement of HA concentration which is accurate, recoveries values were normalized against the recovery value obtained when using Zwittergent 3-14™ 10%, which percentage has been shown in Examples 1 and 2 to provide an accurate measurement (see last column of Table 8). The normalized values of HA recoveries indicate that Zwittergent 3-14™ 5% (100%), Zwittergent 3-14™ 15% (104%) and Zwittergent 3-14™ 20% (104%) allow to reach HA concentrations similar to the HA concentration achieved when using Zwittergent 3-14™ 10%. These results suggest that 5%, 10%, 15% and 20% all represent percentages of Zwittergent 3-14™ providing an accurate measurement of HA concentration in an influenza vaccine comprising an oil-in-water emulsion.

With regard to other detergents, data presented in Table 8 (see the last column) indicate that while 1% is an inappropriate percentage to use, Zwittergent 3-12™ 10% and Empigen™ 10% may also be suitably used in the method according to the present invention.

We claim:

1. A method for performing an immunodiffusion assay in order to determine an influenza virus antigen concentration comprising at least the following steps of:
    (a) preparing one or more test samples comprising the influenza virus antigen adjuvanted with an oil-in-water emulsion,
    (b) treating the test samples with at least 10% (w/v) of a zwitterionic detergent,
    (c) applying the treated test samples to a gel comprising an antibody specific to the influenza virus antigen, and
    (d) allowing the samples to diffuse into the gel.

2. The method according to claim 1, comprising the further step of (e) determining a dimension of precipitation rings formed in the gel by the treated test samples.

3. The method according to claim 2, comprising the further step (f) of preparing and treating reference samples comprising the influenza virus antigen of a known concentration in the same conditions as the test samples, applying the treated reference samples to the gel and determining a dimension of precipitation rings in the gel formed by the treated reference samples.

4. The method according to claim 3, comprising the further step of (g) comparing the dimension determined in step (e) with the dimension determined in step (f) to calculate the influenza virus antigen concentration in the test sample applied in step (c).

5. The method according to claim 4, wherein the concentration of the antigen indicates the stability of the test samples.

6. The method according to claim 5, wherein the concentration of the antigen within the test sample is quantitated after the test sample has been stored for a period of time of at least 7 days.

7. The method according to claim 3, wherein at least one of the test samples and the reference samples comprise a vaccine.

8. The method according to claim 7, wherein the oil-in-water emulsion comprises squalene, alpha-tocopherol and polyoxythethylene sorbitan monoleate.

9. The method according to claim 1, wherein the detergent is n-Tetradecyl-N,N-dimethyl-3-ammonio-1-propanesulfonate.

10. The method according to claim 1, wherein the influenza virus antigen is hemagglutinin (HA).

11. The method according to claim 1, wherein the test sample is an inactivated influenza vaccine.

12. The method according to claim 1, wherein the immunodiffusion assay is a Single Radial Immunodiffusion assay.

13. A method for quantitating hemagglutinin (HA) concentration of a vaccine comprising an influenza virus antigen adjuvanted with an oil-in-water emulsion which comprises at least the following steps of:
    (i) treating the vaccine, or a sample thereof, with at least 10% (w/v) of a detergent,
    (ii) treating reference samples comprising the influenza virus HA antigen of a known concentration with at least 10% (w/v) of a zwitterionic detergent,
    (iii) applying the treated vaccine, or a sample thereof, and the treated reference samples to a gel containing an antibody specific to the influenza virus HA antigen,
    (iv) allowing the samples to diffuse into the gel,
    (v) determining a dimension of precipitation rings in the gel formed by the vaccine, or a sample thereof, and a dimension of precipitation rings formed by the reference samples, and
    (vi) comparing together the dimensions determined in step (v) to calculate the HA concentration in the vaccine, or a sample thereof, applied in step (iii), wherein the steps (i) and (ii) are optionally implemented in absence of any exogenous salt.

14. The method according to claim 13, wherein the oil-in-water emulsion comprises squalene, alpha-tocopherol and polyoxythethylene sorbitan monoleate.

15. The method according to claim 13, wherein the detergent is n-Tetradecyl-N,N-dimethyl-3-ammonio-1-propanesulfonate.

* * * * *